(12) United States Patent
Deng et al.

(10) Patent No.: US 9,629,864 B2
(45) Date of Patent: Apr. 25, 2017

(54) USE OF BAICALIN IN PREPARATION OF DRUGS FOR TREATING ACUTE HEMOLYTIC UREMIC SYNDROME

(71) Applicants: HUBEI WUDANG ANIMAL PHARMACEUTICAL CO., LTD., Shiyan, Hubei (CN); JILIN UNIVERSITY, Changchun, Jilin (CN); TIANJIN INTERNATIONAL JOINT ACADEMY OF BIOMEDICINE, Tianjin (CN)

(72) Inventors: Xuming Deng, Changchun (CN); Zihe Rao, Changchun (CN); Jing Dong, Changchun (CN); Cheng Yang, Changchun (CN); Xiaodi Niu, Changchun (CN); Xuemei Li, Changchun (CN); Yutao Chen, Changchun (CN); Quan Wang, Changchun (CN); Dacheng Wang, Changchun (CN)

(73) Assignees: HUBEI WUDANG ANIMAL PHARMACEUTICAL CO., LTD., Shiyan, Hubei (CN); JILIN UNIVERSITY, Changchun, Jilin (CN); TIANJIN INTERNATIONAL JOINT ACADEMY OF BIOMEDICINE, Tianjin (CN)

( * ) Notice: Subject to any disclaimer, the term of this patent is extended or adjusted under 35 U.S.C. 154(b) by 0 days.

(21) Appl. No.: 15/022,737

(22) PCT Filed: Apr. 29, 2014

(86) PCT No.: PCT/CN2014/076442
§ 371 (c)(1),
(2) Date: Mar. 17, 2016

(87) PCT Pub. No.: WO2015/039442
PCT Pub. Date: Mar. 26, 2015

(65) Prior Publication Data
US 2016/0235777 A1    Aug. 18, 2016

(30) Foreign Application Priority Data

Sep. 18, 2013  (CN) .......................... 2013 1 0428271
Apr. 23, 2014  (CN) .......................... 2014 1 0166500

(51) Int. Cl.
*A61K 31/7048* (2006.01)
(52) U.S. Cl.
CPC .............................. *A61K 31/7048* (2013.01)
(58) Field of Classification Search
None
See application file for complete search history.

(56) References Cited

U.S. PATENT DOCUMENTS

2003/0091651 A1* 5/2003 Xu .................. A23L 1/3004
424/539

FOREIGN PATENT DOCUMENTS

| CN | 1501083 A | 6/2004 |
| CN | 1511540 A | 7/2004 |
| CN | 103006679 A | 4/2013 |

OTHER PUBLICATIONS

"Research progress in pharmacological effects of baicalin," Tianjin Pharmacy, 2012, vol. 24, No. 3, pp. 61-64.
Boerlin, P., "The Relationship between Virulence Factors of Shiga Toxin—producing *E. Coli* and Human Diseases," J. Clin. Microbiol., Aug. 31, 1999, vol. 37, No. 3, pp. 497-503.
Chinese Office Action for Appl. No. 201410166500.2 dated Aug. 31, 2015 (w/ English translation).
Chinese Office Action for Appl. No. 201410166500.2 dated May 11, 2016 (w/ English translation).
Tao, F., "Plant Antibacterial Agent—A Study on Extration of Baicalin and Its Antimicrobial Activity," Textile Dyeing and Finishing Journal, Jan. 31, 2008, vol. 30, No. 1, pp. 1-6.

* cited by examiner

*Primary Examiner* — Traviss C McIntosh, III
(74) *Attorney, Agent, or Firm* — Birch, Stewart, Kolasch & Birch, LLP

(57) ABSTRACT

Disclosed is a use of baicalin in the preparation of drugs for treating acute hemolytic uremic syndrome.

6 Claims, 3 Drawing Sheets

USE OF BAICALIN IN PREPARATION OF DRUGS FOR TREATING ACUTE HEMOLYTIC UREMIC SYNDROME

FIELD OF THE INVENTION

The present invention belongs to the field of medicine, and in particular relates to a use of baicalin in the preparation of drugs for treating acute hemolytic uremic syndrome.

BACKGROUND OF THE INVENTION

Baicalin is a flavonoid extracted and isolated from the root of Scutellaria baicalensis Georgi, and has significant antifungal activity, and especially acts selectively on yeast-type fungi, with a minimal inhibitory concentration (MIC) in a range of 70-100 μg/ml. However, there has been no report on the use of baicalin in the treatment of acute hemolytic uremic syndrome caused by Escherichia coli.

Acute hemolytic uremic syndrome is a condition generally caused by type 2 Shiga toxin secreted from Escherichia coli, and renal injury is generally one of the serious complications. This syndrome predominantly occurs in the elderly and children, with an extremely high mortality rate. In recent years, massive use of antibiotics has resulted in more and more drug-resistant strains of Escherichia coli, so treatment of Escherichia coli infection has been confronted with the stern challenge in clinical practice, but antibiotics can usually stimulate the secretion of type 2 Shiga toxin from drug-resistant Escherichia coli, which in turn leads to further progression of diseases. Therefore, it is imperative to seek novel and safe therapeutic drugs. Baicalin is a constituent derived from traditional Chinese medicinal materials, such as the root of Scutellaria baicalensis Georgi and the seed of Oroxylum indicum. Research in the present invention has proved that baicalin has a better curative effect on acute hemolytic uremic syndrome caused by type 2 Shiga toxin from Escherichia coli, especially by type 2 Shiga toxin from drug-resistant Escherichia coli.

SUMMARY OF THE INVENTION

Molecular structure of baicalin is as follows:

The present invention has found that baicalin has a better curative effect on acute hemolytic uremic syndrome caused by type 2 Shiga toxin from Escherichia coli, especially has a much better curative effect on acute hemolytic uremic syndrome caused by type 2 Shiga toxin from drug-resistant Escherichia coli.

Meanwhile, the present invention provides a use of baicalin in the preparation of drugs for treating acute hemolytic uremic syndrome.

Preferably, the technical solution of the present invention refers to a use of baicalin in the preparation of drugs for treating acute hemolytic uremic syndrome caused by type 2 Shiga toxin from Escherichia coli.

In the present invention, baicalin can be made into various kinds of dosage forms after being added with pharmaceutically acceptable excipients. The drugs of the present invention comprise any pharmaceutically acceptable dosage form.

Preferably, baicalin can be made into dosage forms such as injections, capsules, tablets and powders for injection.

Compared with antibiotic treatment, treatment with baicalin has advantages of no drug-resistance and high cure rate.

DETAILED DESCRIPTION OF THE EMBODIMENTS

The therapeutic effects of baicalin on the infection with type 2 Shiga toxin were confirmed by protective effects on Hela cells and the mouse model of acute hemolytic uremic syndrome.

Example 1

Protective Effects of Baicalin on Hela Cells

Cultured Hela cells were plated into 96-well cell culture plates at a density of 15000 cells per well, after 24 h incubation to allow complete adherence to surfaces, 50 pg of purified type 2 Shiga toxin was added to each well, and different concentrations of baicalin solution were added, then the cells were incubated in $CO_2$ incubator. After incubation for 72 h, the culture medium supernatants were collected by centrifugation for detecting lactate dehydrogenase release amount. The protective effects of baicalin on the cells were evaluated by lactate dehydrogenase release. The result showed that baicalin significantly inhibited the cytotoxicity of Hela cells caused by type 2 Shiga toxin, in a dose-dependent manner. Survival rates of Hela cells after adding different concentrations of baicalin are shown in Table 1 below:

TABLE 1

Inhibitory effects of baicalin on the cytotoxicity of Hela cells caused by type 2 Shiga toxin.

| Baicalin (μg/ml) | Survival rate (%) |
|---|---|
| 0 | 24.34 |
| 4 | 38.63 |
| 8 | 50.22 |
| 16 | 57.14 |
| 32 | 75.14 |

Example 2

Figure 1:
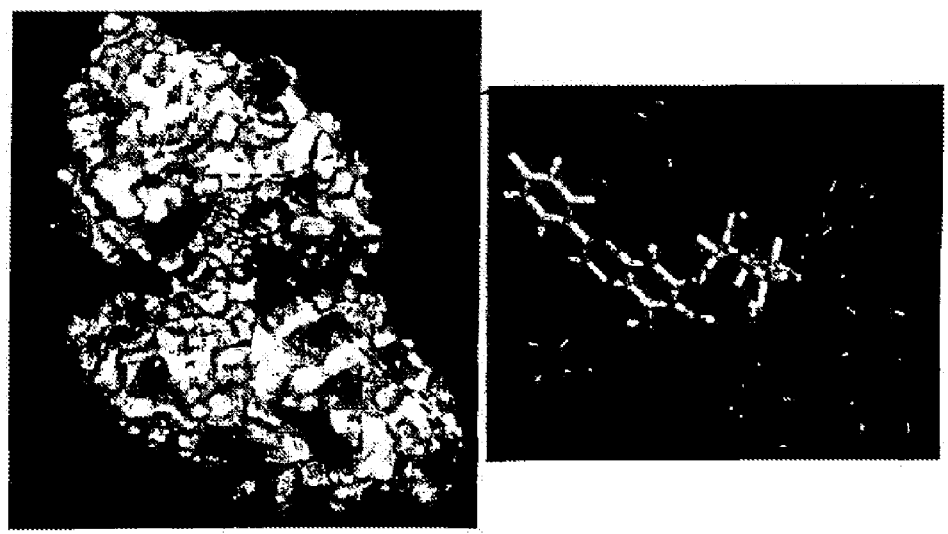
FIG. 1 shows molecular docking images from which it finds that baicalin binds to the enzymatic active center of subunit Stx2 A (The figure at the left indicates the binding pattern of baicalin to Stx2, and the figure at the right indicates the binding site of baicalin to Stx2).
Figure 2:
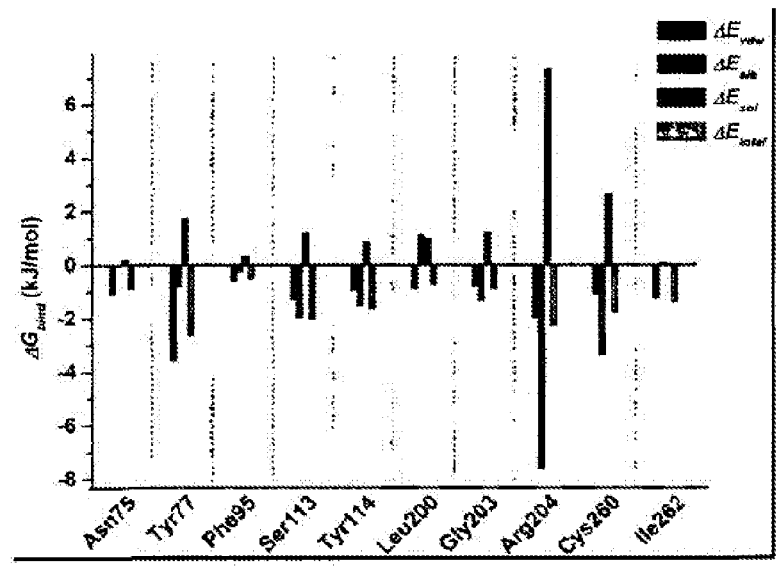
FIG. 2 shows an analysis on free energy contribution of a complex system, wherein the horizontal axis shows different types of amino acids, and the vertical axis shows free energy changes; Etotal denotes the total binding energy, $E_{vdw}$ denotes van der Waals force, $E_{ele}$ denotes electrostatic force, and $E_{sol}$ denotes energy of non-polar solvation.

Analysis on Mechanisms of Baicalin Against Type 2 Shiga Toxin and Target Validation Through molecular simulation and molecular docking, it was found that baicalin could bind to the active pocket of type 2 Shiga toxin, thereby inhibiting the exhibition of its activity. By decomposing the free energy of the complex system, it was also found that Tyrosine 77 and Arginine 204 were the two amino acids that made a greater contribution to the free energy of the complex system. The obtained data were further validated using site-directed mutagenesis and fluorescence quenching, and the results showed that computer simulation results were consistent with validation results. Baicalin bound to the amino acids at sites 77 and 204 in type 2 Shiga toxin, resulting in the loss of enzymatic activity, thereby inhibiting the exhibition of its activity. The binding site of baicalin to type 2 Shiga toxin is shown in FIG. 1, and an analysis on binding energy is shown in FIG. 2.

Example 3

Structural Biology Target Validation

Figure 3:
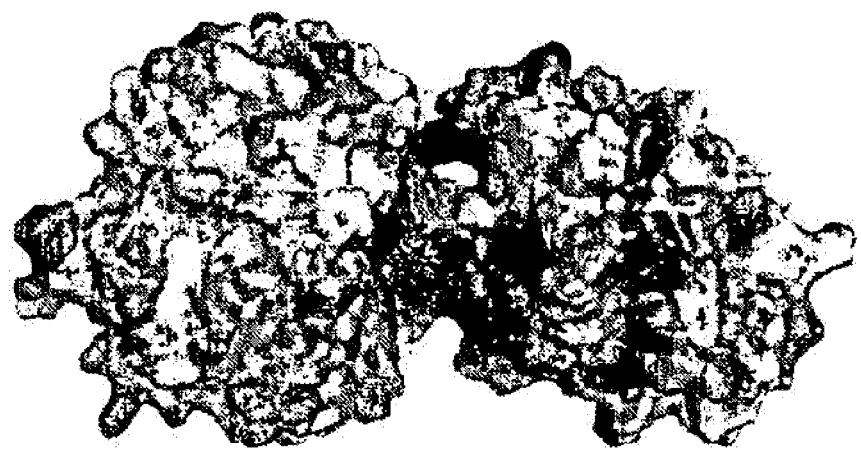
FIG. 3 shows baicalin induces subunit A of ricin to form a polymer.

In this study, a crystal of subunit A of ricin protein which is similar to type 2 Shiga toxin in structure and function was obtained, and then the crystal structure of the complex of subunit A of ricin with baicalin was resolved. By structural analysis it was found that baicalin could induce subunit A of ricin to form a polymer, resulting in the loss of activity (FIG. 3), and the binding sites of baicalin to subunit A of ricin were R189, T190, R193, Y194, R235 and R258. It was also found by sequence alignment that the binding sites of baicalin to type 2 Shiga toxin were R179, Q180, S183, E184 and V218.

Example 4

Study on Experimental Acology of Acute Hemolytic Uremic Syndrome in Mice 4.1 Mouse Model of Acute Hemolytic Uremic Syndrome.

Male BALB/C mice, weighing 18-22 g, were anesthetized with ethyl ether, and were given purified type 2 Shiga toxin protein by intraperitoneal injection, then the mice were kept lying on their back until they regained consciousness. In this way, a mouse model of acute hemolytic uremic syndrome was successfully established. For the survival rate experiment, pathology experiment and renal function evaluation experiment, the mice were given 50 ng of purified type 2 Shiga toxin protein.

4.2 Protective Rate Test.

Figure 4:
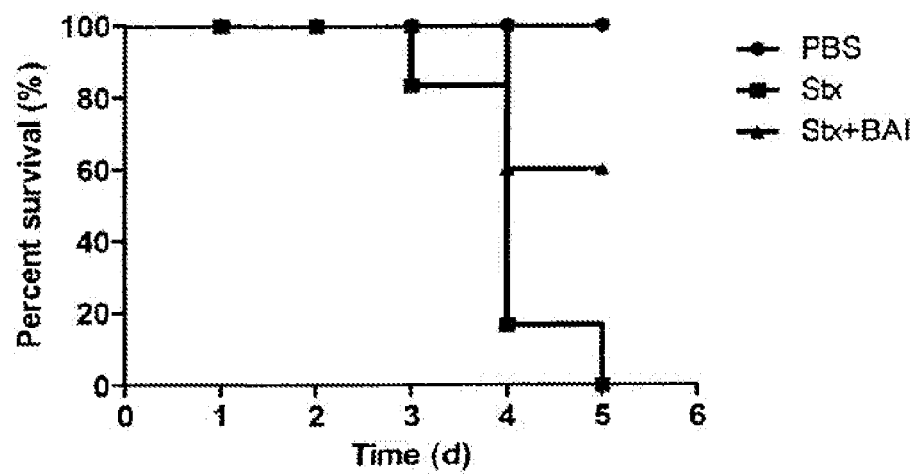
FIG. 4 shows effect of baicalin on the survival rate of mice with acute uremic syndrome, wherein the horizontal coordinate shows the observation time, and the vertical coordinate shows the survival rate; the unit of time is day, abbreviated as "d", PBS denotes negative control group, Stx denotes infected group without drug administration, and Stx+BAI denotes drug administration group.

For the protective rate test, male BALB/c mice were randomly assigned into 3 experimental groups (20 in each): the normal control group was treated with sterilized PBS alone, Stx denoted the infected group without drug administration, and Stx+BAI denoted the treatment group. 6 h after injection with type 2 Shiga toxin protein, mice in the drug administration group were given subcutaneous injection of 200 mg/kg baicalin, one dose every 6 h for a total of 96 h. After injection with the toxin, mice in the model control group (Stx group) were given 100 μl of sterilized PBS. Survival rates in all groups were counted. The results showed that the survival rates of mice with acute hemolytic uremic syndrome were significantly increased after baicalin treatment, as shown in FIG. 4.

4.3 Histopathological Experiment.

Figure 5:
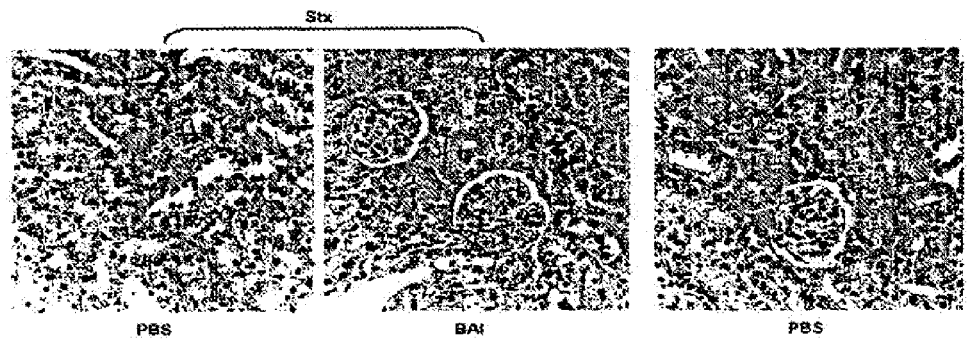
FIG. 5 shows histopathological changes in kidneys of mice with acute uremic syndrome after injection of baicalin, wherein PBS denotes negative control group, Stx denotes infected group without drug administration, and Stx+BAI denotes drug administration group.

For this experiment, male BALB/c mice were randomly assigned into 3 experimental groups (20 in each): the normal control group was treated with sterilized PBS alone, Stx denoted the infected group without drug administration, and Stx+BAI denoted the treatment group. 6 h after injection with type 2 Shiga toxin protein, mice in the drug administration group were given subcutaneous injection of 200 mg/kg baicalin, one dose every 6 h for a total of 72 h. After injection with the toxin, mice in the model control group (Stx group) were given 100 μl of sterilized PBS (10 mice in each group). 72 h after the infection, mice were euthanized under anesthesia and kidneys were enucleated for making pathological sections, then pathological changes were observed. The results showed that in mice of the model control group, renal hemorrhage appeared, large numbers of epithelial cells shed from renal tubules, and renal glomeruli disappeared; while in mice of the drug administration group, only a minor hemorrhage existed in the kidney tissue, and there was no significant difference compared with mice in normal group, as shown in FIG. 5.

4.4 Renal Function Evaluation Experiment.

Figure 6:
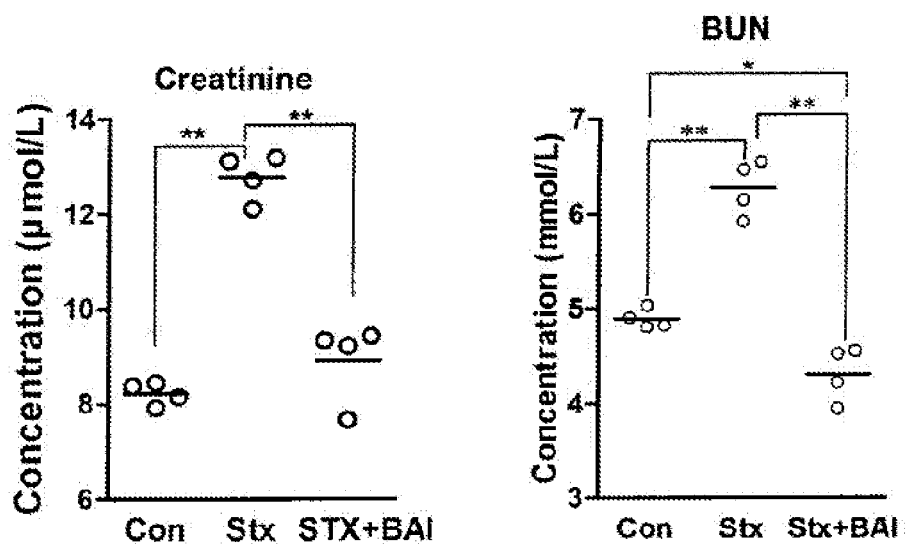
FIG. 6 shows effect of baicalin on the renal function of mice with acute uremic syndrome, wherein the horizontal coordinate shows the treatment ways, and the vertical coordinate shows the concentrations; Con denotes negative control group, Stx+BAI denotes drug administration group, and Stx denotes infected group without drug administration.

For this experiment, male BALB/c mice were randomly assigned into 3 experimental groups (20 in each): the normal control group was treated with sterilized PBS alone, Stx denoted the infected group without drug administration, and Stx+BAI denoted the treatment group. 6 h after injection with type 2 Shiga toxin protein, mice in the drug administration group were given subcutaneous injection of 200 mg/kg baicalin, one dose every 6 h for a total of 72 h. After injection with the toxin, mice in the model control group (Stx group) were given 100 μl of sterilized PBS (10 mice in each group). The improvement of baicalin on the renal function of the model mice was evaluated by detecting the contents of creatinine and blood urea nitrogen (BUN) in mouse serum. The results showed that there was no significant difference in the contents of creatinine and BUN between mice in the drug administration group and the normal control group ($P>0.05$), while there was an extremely significant difference between mice in the model control group and the normal control group ($P<0.01$), as shown in FIG. 6.

The invention claimed is:

1. A method for treating acute hemolytic uremic syndrome, comprising
administering an effective amount of baicalin to a patient in need thereof.

2. The method according to claim 1, wherein the acute hemolytic uremic syndrome is caused by type 2 Shiga toxin from *Escherichia coli*.

3. The method according to claim 1, wherein the baicalin is prepared into a pharmaceutically acceptable dosage form.

4. The method according to claim 2, wherein the baicalin is prepared into a pharmaceutically acceptable dosage form.

5. The method according to claim 3, wherein the dosage form is selected from the group consisting of injections, capsules, tablets and powders for injection.

6. The method according to claim 4, wherein the dosage form is selected from the group consisting of injections, capsules, tablets and powders for injection.

\* \* \* \* \*